United States Patent [19]

Fischer et al.

[11] Patent Number: 5,001,243

[45] Date of Patent: Mar. 19, 1991

[54] SUBSTITUTED NAPHTHACENE-5,12-DIONES

[75] Inventors: Walter Fischer, Reinach; Marcus Baumann, Basle, both of Switzerland; Jürgen Finter, Freiburg, Fed. Rep. of Germany; Vratislav Kvita, Reinach, Switzerland; Carl W. Mayer, Riehen, Switzerland; Manfred Rembold, Aesch, Switzerland; Martin Roth, Giffers, Switzerland

[73] Assignee: Ciba-Geigy Corporation, Ardsley, N.Y.

[21] Appl. No.: 356,828

[22] Filed: May 24, 1989

[30] Foreign Application Priority Data

May 27, 1988 [CH] Switzerland .................. 2008/88
Jul. 19, 1988 [CH] Switzerland .................. 2756/88

[51] Int. Cl.$^5$ ..................... C07C 50/22; C07C 50/36
[52] U.S. Cl. ................................ 552/201; 552/202; 552/203
[58] Field of Search ................ 552/201, 202, 203

[56] References Cited

U.S. PATENT DOCUMENTS 3,941,759  3/1976  Taylor et al. ............... 260/92.8

OTHER PUBLICATIONS

Farina et al., An Quim Ser C. vol. 81 (2) pp. 133-138 (1985).
Derwent Abstract of Japanese 49081-440 (1974).

Primary Examiner—Richard L. Raymond
Assistant Examiner—Raymond Covington
Attorney, Agent, or Firm—Michael W. Glynn; Stephen O'Brien

[57] ABSTRACT

Naphthacene-5,12-diones which are substituted by at least one organic thio radical are not only photoinitiators for the photopolymerization but also sensitizers for the photodimerization of ethylenically unsaturated compounds. Compositions made of these naphthacene-5,12-diones and ethylenically unsaturated compounds are suitable for the preparation of printing inks, paints, printing plates, resist materials or as image recording material.

10 Claims, No Drawings

SUBSTITUTED NAPHTHACENE-5, 12-DIONES

The invention relates to naphthacene-5,12-diones substituted by an organic thio radical; to a process for their preparation by Diels-Alder reaction of benzocyclobutene 1,2-dihalides with appropriately substituted naphtho-1,4-quinones; to a composition polymerizable by radiation containing such a naphthacene-5,12-dione as photoinitiator or sensitizer; and to the use of this composition for the preparation of paints, printing inks, printing plates, resist materials and as image recording material and coating material.

JP-OS No. 49/081440 has described 1-hydroxynaphthacene-5,12-diones substituted in the 4-position by phenylthio, p-toluylthio or p-chlorophenylthio as fluorescent dyes for plastics. U.S. Pat. No. 3,941,759 describes naphthacene-5,12-dione as sensitizer component for plastics decomposable by UV light.

It has now been found that naphthacene-5,12-diones substituted by an organic thio radical are excellent photoinitiators for photopolymerization and, at the same time, excellent sensitizers for the photodimerization of ethylenically unsaturated compounds.

The invention relates to compounds of the formula I

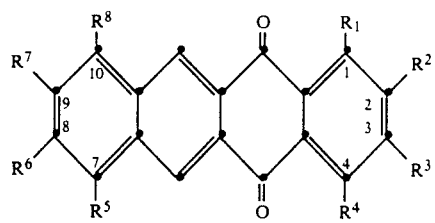

in which
$R^1$, $R^2$, $R^3$, $R^4$, $R^5$, $R^6$, $R^7$ and $R^8$, independently of one another, are H, —CN, —NO$_2$, halogen, —NR$^{10}$R$^{11}$, —COOR$^9$, —CONR$^{10}$R$^{11}$, —SiR$^{13}$R$^{14}$R$^{15}$, or unsubstituted or —OH—, —CN—, —NR$^{10}$R$^{11}$—, halogen-, C$_1$-C$_{18}$alkyl, -alkoxy- or -alkylthio-, —COOR$^9$— or —CONR$^{10}$R$^{11}$-substituted C$_1$-C$_{20}$alkyl(X)$_p$, C$_2$-C$_{20}$alkenyl(X)$_p$, C$_2$-C$_{18}$alkynyl(X)$_p$, C$_3$-C$_8$cycloalkyl(X)$_p$, C$_6$-C$_{12}$aryl(X)$_p$ or C$_7$-C$_{14}$aralkyl(X)$_p$ or —Y(C$_m$H$_{2m}$O)$_n$R$^{12}$;

X is O, S, SO or SO$_2$ and p is 0 or 1; Y is O or S; $R^9$ is H or the radical minus a hydroxyl hydrogen atom of a C$_1$-C$_{20}$alcohol and $R^{10}$ and $R^{11}$, independently of one another, are H, C$_1$-C$_{18}$alkyl, phenyl, benzyl, cyclo-pentyl, cyclohexyl, C$_2$-C$_{12}$mono- or C$_2$-C$_{12}$dihydroxyalkyl, (C$_m$H$_{2m}$O)$_n$R$^{12}$ or $R^{10}$ and $R^{11}$ together are tetra- or pentamethylene or 3-oxa-1,5-pentylene; m is 2 to 6, n is 2 to 20; $R^{12}$ is H or C$_1$-C$_{12}$alkyl; $R^{13}$, $R^{14}$ and $R^{15}$, independently of one another are C$_1$-C$_{12}$alkyl; at least one of the radicals $R^2$, $R^3$, $R^5$, $R^6$, $R^7$ and $R^8$ being a thio radical.

The groups $R^1$ to $R^8$ can be mono- or polysubstituted, preferably mono- to hexasubstituted, in particular mono- to trisubstituted and in particular mono- or disubstituted.

A halogen substituent is preferably —F, —Cl and —Br. Where the substituent is alkyl, alkoxy or alkylthio, these groups can be linear or branched and preferably contain 1 to 12, in particular 1 to 6 C atoms. Some examples are methyl, ethyl, the isomers of propyl, butyl, pentyl, hexyl, heptyl, octyl, nonyl, decyl, undecyl, dodecyl, tetradecyl, octadecyl, and the corresponding alkoxy and alkylthio groups.

The substituents can be radicals of the formula —NR$^{10}$R$^{11}$ or —CONR$^{10}$R$^{11}$. In these, $R^{10}$ and $R^{11}$ as alkyl can be linear or branched and preferably contain 1 to 12, in particular 1 to 8 C atoms. $R^{10}$ and $R^{11}$ as monohydroxyalkyl preferably contain 2 to 6 C atoms; they can be linear or branched hydroxyalkyl. Some examples are 2-hydroxyethyl, 2- or 3-hydroxyprop-1-yl, 2-, 3- or 4-hydroxybut-1-yl, 2-hydroxybut-3-yl, hydroxypentyl and hydroxyhexyl. $R^{10}$ and $R^{11}$ as dihydroxyalkyl can be linear or branched and preferably contain 3 to 6 C atoms. Examples are 1,2-dihydroxyprop-3yl, 1,2-dihydroxybut-3- or -4-yl. $R^{10}$ and $R^{11}$ can be a radical of the formula (C$_m$H$_{2m}$O)$_n$R$^{12}$ in which m is preferably a number from 2 to 4, in particular 2 or 3, n is preferably a number from 2 to 12, in particular 2 to 6, and $R^{12}$ is H or linear or branched alkyl preferably having 1 to 6 C atoms.

The substituents can be a —COOR$^9$ group in which $R^9$ is H or the radical minus a hydroxyl hydrogen atom of an alcohol preferably having 1 to 12, in particular 1 to 8 C atoms. For example, $R^9$ can be linear or branched C$_1$-C$_{20}$, preferably C$_1$-C$_{12}$ and in particular C$_1$-C$_8$alkyl, cyclopentyl, cyclohexyl, unsubstituted or C$_1$-C$_{12}$alkyl-substituted phenyl or benzyl or the radical of the formula (—C$_m$H$_{2m}$O—)$_n$R$^{12}$ in which $R^{12}$, m and n are as defined above, including the preferences.

In a preferred embodiment, the substituents for $R^1$ to $R^8$ are —OH, —F, —Cl, —Br, —NR$^{10}$R$^{11}$, C$_1$-C$_{12}$alkyl, C$_1$-C$_{12}$alkoxy, C$_1$-C$_{12}$alkylthio or —COOR$^9$ in which $R^9$ is H or C$_1$-C$_{18}$alkyl and $R^{10}$ and $R^{11}$, independently of one another, are H, C$_1$-C$_{18}$alkyl, —CH$_2$CH$_2$OH, —CH$_2$CH(OH)CH$_3$, —CH$_2$CHOHCH$_2$OH, or (C$_m$H$_{2m}$O)$_n$R$^{12}$ in which m is 2 or 3, n is a number from 2 to 6 and $R^{12}$ is H or C$_1$-C$_{12}$alkyl.

The group $R^2$ is preferably a thio radical $R^{16}$—S— in which $R^{16}$ is unsubstituted or, as defined above, substituted C$_1$-C$_{20}$alkyl, C$_2$-C$_{20}$alkenyl, C$_2$-C$_{20}$alkynyl, C$_3$-C$_8$cycloalkyl, C$_6$-C$_{12}$aryl or C$_7$-C$_{12}$aralkyl or is (C$_m$H$_{2m}$O)$_n$R$^{12}$. In a preferred embodiment, $R^2$, or $R^2$ and $R^3$, or $R^6$, or $R^7$, or $R^6$ and $R^7$, or $R^2$ and $R^6$ or $R^7$, or $R^2$, $R^3$ and $R^6$ or $R^7$, or $R^2$, $R^3$, $R^6$ and $R^7$ are a thio radical or —S(C$_m$H$_{2m}$O)$_n$R$^{12}$. $R^1$, $R^4$, $R^5$ and $R^8$ are in particular H.

$R^{16}$, when having the meaning of alkyl, preferably contains 1 to 12, especially 1 to 8 and in particular 1 to 4 C atoms and can be linear or branched. Examples have been mentioned above. $R^{16}$ as alkenyl can be linear or branched and preferably contains 3 to 12, especially 3 to 6 C atoms and preferably contains a terminal double bond. Examples are allyl, but-1-en-4-yl, but-2-en-4-yl, pent-1-en-5-yl and hex-1-en-6-yl. $R^{16}$ as alkynyl can be linear or branched and preferably contains 3 to 12, especially 3 to 6 C atoms and preferably a terminal triple bond. $R^{16}$ as cycloalkyl preferably contains 4 to 7, especially 5 or 6 ring C atoms.

Examples of cycloalkyl are cyclopropyl, cyclobutyl, cyclopentyl, cyclohexyl, cycloheptyl and cyclooctyl. $R^{16}$ as aryl is, for example, naphthyl and especially phenyl, and as aralkyl especially phenyl-C$_x$H$_{2x}$— in which x is a number from 1 to 6, especially 1 or 2. $R^{16}$ can also be the radical of the formula (C$_m$H$_{2m}$O)$_n$R$^{12}$ in which $R^{12}$, m and n are as defined above, including the preferences.

A preferred embodiment comprises those compounds of the formula I in which $R^{16}$ is unsubstituted or substituted $C_1$–$C_{20}$alkyl, cyclopentyl, cyclohexyl, phenyl or benzyl or $(C_mH_{2m}O)_nR^{12}$, in which m is a number from 2 to 4, n a number from 2 to 12 and $R^{12}$ is H or $C_1$–$C_{12}$alkyl.

Another preferred embodiment comprises those compounds of the formula I in which $R^{16}$ is unsubstituted or —OH—, —NR$^{10}$R$^{11}$—, $C_1$–$C_{18}$alkoxy-, —COOR$^9$— or —CONR$^{10}$R$^{11}$—substituted $C_1$–$C_{18}$alkyl or $(C_mH_{2m}O)_nR^{12}$, in which m is 2 or 3 and n is a number from 2 to 6 and $R^{12}$ is H or $C_1$–$C_6$alkyl.

A preferred embodiment also comprises those compounds of the formula I in which $R^{16}$ is unsubstituted $C_1$–$C_{18}$alkyl or $C_1$–$C_{12}$alkoxy- or —COOR$^9$—substituted $C_1$ to $C_6$alkyl, in which $R^9$ is $C_1$–$C_{12}$alkyl, or is —OH— or —NR$^{10}$R$^{11}$—substituted $C_2$–$C_6$alkyl, in which $R^{10}$ and $R^{11}$ are H or $C_1$–$C_{12}$alkyl.

Very particular preference is given to those compounds of the formula I in which $R^{16}$ is $C_1$–$C_{12}$alkyl, $C_6$–$C_{12}$aryl, $C_7$–$C_{18}$alkaryl, —CH$_2$CH$_2$OH, —CH$_2$CHOHCH$_2$OH, —CH$_2$COOR$^9$ or —CH$_2$CH$_2$COOR$^9$ and $R^9$ is as defined above, including the preferences. In this case, $R^1$ and $R^3$ to $R^8$ are particularly preferably H.

$R^1$ and $R^3$ to $R^8$ as halogen are preferably —F, —Cl or —Br. $R^1$ and $R^3$ to $R^8$ can independently be a radical of the formula —COOR$^9$, —NR$^{10}$R$^{11}$ or —CONR$^{10}$R$^{11}$, in which in this case, too, the preferences given above for these radicals independently apply to $R^9$, $R^{10}$ and $R^{11}$.

$R^1$ and $R^3$ to $R^8$ can be a radical of the formula —SiR$^{13}$R$^{14}$R$^{15}$ in which $R^{13}$, $R^{14}$ and $R^{15}$ are linear or branched alkyl and which preferably contains 1 to 8, especially 1 to 4 C atoms. Some examples are trimethyl-, ethyldimethyl-, triethyl-, tri-n- or tri-i-propyl-, n-propyldimethyl-, tri-n-butyl-, n-butyldimethyl-, t-butyldimethyl- and (1,1,2,2-tetramethylethyl)dimethylsilyl.

$R^1$ and $R^3$ to $R^8$ can be unsubstituted or substituted, linear or branched $C_1$–$C_{20}$, preferably $C_1$–$C_{18}$, especially $C_1$–$C_{12}$ and in particular $C_1$–$C_6$alkyl(X)$_p$ in which p is 0 or 1 and X is O, S, SO or SO$_2$, especially O or S. Some examples are methyl, ethyl, and the isomers of propyl, butyl, pentyl, hexyl, heptyl, octyl, nonyl, decyl, undecyl, dodecyl, tetradecyl, hexadecyl, octadecyl, eicosyl and the corresponding alkoxy, alkylthio, alkylsulfinyl, and alkylsulfonyl radicals, 2-hydroxyethyloxy or -thio, 1,2-dihydroxypropyloxy, 2-aminoethyloxy or -thio, 4-hydroxybutyloxy, 6-hydroxyhexyloxy, 2-hydroxydecyloxy, di(methoxycarbonyl)methyl, 1,1-di(methoxycarbonyl)ethyl, cyano(methoxycarbonyl)methyl, carboxymethyl, trifluoromethyl, carbamoylmethyl, (ethoxycarbonyl)methoxy.

$R^1$ and $R^3$ to $R^8$ can be unsubstituted or substituted $C_2$–$C_{18}$, preferably $C_2$–$C_{12}$ and especially $C_2$–$C_6$alkenyl(X)$_p$ or -alkynyl(X)$_p$, which can be linear or branched and in which p is 0 or 1 and X is O, S, SO or SO$_2$, preferably S or O. When p is 1, the alkenyl or alkynyl group is preferably separated from the benzene rings in the compounds of the formula I by at least one CH$_2$ group. Some examples are vinyl, ethinyl and allyl, propargyl, crotonyl, 1-buten-3- or 4-yl, 1-or 2-penten-5-yl, 1-, 2- or 3-hexen-6-yl, 1-hepten-7-yl, 1-octen-8-yl, 1-nonen-9-yl, 1-decen-10-yl, 1-undecen-11-yl, 1-dodecen-12-yl, and the corresponding alken- and alkinoxy, -thio, -sulfinyl and sulfonyl radicals.

$R^1$ and $R^3$ to $R^8$ can be unsubstituted or substituted $C_3$–$C_8$, preferably $C_4$–$C_7$, and especially $C_5$ or $C_6$cycloalkyl(X)$_p$ in which p is 0 or 1 and X is S, O, SO or SO$_2$. X is preferably O or S. Examples are cyclopentyl, cyclohexyl, methylcyclohexyl, cyclohexyloxy and cyclohexylthio.

$R^1$ and $R^3$ to $R^8$ can be substituted or unsubstituted $C_6$–$C_{12}$aryl(X)$_p$ or $C_6$–$C_{12}$aralkyl(X)$_p$ in which X is O, S, SO or SO$_2$, especially O or S, and p is 0 or 1, and the aryl is preferably naphthyl and especially phenyl. Aralkyl preferably corresponds to phenyl(C$_z$H$_{2z}$) where z is a number from 1 to 6, especially 1 to 4, and is in particular benzyl. Examples are phenyl, benzyl, methylphenyl, ethylphenyl, dodecylphenyl, methylbenzyl, phenylthio, phenoxy, chlorophenoxy, methoxyphenoxy, methylthiophenoxy, methoxyphenylthio, benzylthio, methoxybenzylthio and methylbenzylthio.

$R^1$ and $R^3$ to $R^8$ can be a radical of the formula —Y(C$_m$H$_{2m}$O)$_n$R$^{12}$ in which Y is O or S and m, n and $R^{12}$ are as defined above for the group (C$_m$H$_{2m}$O)$_n$R$^{12}$, including the preferences. The C$_m$H$_{2m}$ group is especially —CH$_2$CH$_2$—, —CH$_2$CH$_2$CH$_2$— or —CH$_2$CHCH$_3$—. Some examples are —O(—CH$_2$CH$_2$O—)$_n$R$^{12}$, —S(CH$_2$CH$_2$O)$_n$R$^{12}$, —O(CH$_2$CHCH$_3$O)$_n$R$^{12}$ and —S(CH$_2$CHCH$_3$O)$_n$R$^{12}$, in which n is 2, 3, 4, 5, 6, 7, 8, 9, 10, 11 or 12 and $R^{12}$ is H, methyl, ethyl, n- or i-propyl, n-, i- or t-butyl, pentyl or hexyl.

$R^2$, $R^3$, and $R^5$ to $R^8$, especially $R^2$, $R^3$, $R^6$ and/or $R^7$ as a thio radical are preferably $C_1$–$C_{12}$alkylthio, phenylthio, benzylthio, $C_1$–$C_4$alkylphenylthio or -benzylthio, $C_1$–$C_4$alkoxyphenylthio or -benzylthio, halogen-, especially fluoro-, chloro- or bromophenylthio or -benzylthio, —SCH$_2$CH$_2$OH, —SCH$_2$CHOHCH$_2$OH, —SCH$_2$COOR$^9$ and —SCH$_2$CH$_2$COOR$^9$ where $R^9$ is as defined above, or —S(C$_m$H$_{2m}$O)$_n$R$^{12}$ in which m is 2 or 3, n is 2 to 20 and $R^{12}$ is H or $C_1$–$C_{12}$alkyl.

A preferred embodiment comprises those compounds of the formula I in which $R^1$ and $R^3$ to $R^8$, independently of one another, are H, —CN, —NO$_2$, —F, —Cl, —Br, —COOR$^9$, —NR$^{10}$R$^{11}$, —CONR$^{10}$R$^{11}$, in which $R^9$ is H or $C_1$–$C_{12}$alkyl and $R^{10}$ and $R^{11}$, independently of one another, are H, $C_1$–$C_{12}$alkyl, —CH$_2$CH$_2$OH, —CH$_2$CH(OH)CH$_3$, —CH$_2$CHOHCH$_2$OH or (C$_m$H$_{2m}$O)$_n$R$^{12}$ where m is equal to 2 or 3, n is equal to a number from 2 to 12 and $R^{12}$ is H or $C_1$–$C_{12}$alkyl, or —SiR$^{13}$R$^{14}$R$^{15}$ where $R^{13}$, $R^{14}$ and $R^{15}$ are $C_1$–$C_4$alkyl, or unsubstituted or substituted $C_1$–$C_{18}$alkyl(X)$_p$, $C_6$H$_5$(X)$_p$ or $C_6$H$_5$CH$_2$(X)$_p$ in which X is O or S and p is 0 or 1, or —Y(C$_m$H$_{2m}$O)$_n$R$^{12}$ in which Y is O or S, m is 2 or 3, n is a number from 2 to 12 and $R^{12}$ is H or $C_1$–$C_{12}$alkyl.

In another preferred embodiment, $R^1$ is H, —CF$_3$, —OH, $C_1$–$C_{18}$alkyl, unsubstituted or —OH—substituted $C_1$–$C_{18}$alkoxy, unsubstituted or halogen-, $C_1$–$C_6$alkyl- or -alkoxy-substituted $C_6$–$C_{10}$aryloxy, $C_7$–$C_{10}$aralkyloxy or —COOR$^9$ where $R^9$ is a $C_1$–$C_{20}$alcohol minus the hydroxyl hydrogen atom. $R^1$ is especially H.

In a further preferred embodiment, $R^4$, $R^5$ and $R^8$ are H. $R^1$, $R^4$, $R^5$ and $R^8$ are especially H.

Preference is also given to compounds of the formula I in which $R^3$, or $R^3$ and $R^6$ or $R^7$, or $R^3$, $R^6$ and $R^7$ are $R^{16}$S—; or in which $R^1$, $R^4$, $R^5$ and $R^8$ are H, $R^2$, $R^3$ or both are —SR$^{16}$, and $R^6$ and $R^7$ are H, or $R^2$, $R^6$ or $R^7$ are —SR$^{16}$, and $R^3$ and $R^7$ or $R^3$ and $R^6$ are H; or in which $R^1$ and $R^3$ to $R^8$ are H and $R^{16}$ is as defined above.

The invention further relates to a process for the preparation of compounds of the formula I, which comprises reacting in a Diels-Alder reaction a compound of the formula II

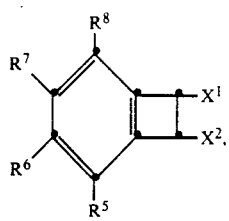

(II)

in which $R^5$, $R^6$, $R^7$ and $R^8$ are as defined above and $X^1$ and $X^2$, independently of one another, are —Cl, —Br or —I with elimination of $HX^1$ and $HX^2$ with a compound of the formula III

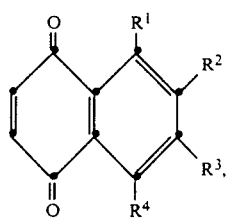

(III)

in which $R^1$, $R^2$, $R^3$ and $R^4$ are as defined above.

The reaction is advantageously carried out at temperatures of 50° to 250° C., preferably 80° to 200° C. Advantageously, an inert solvent is used, for example a polar aprotic solvent. Some examples are aromatic hydrocarbons (benzene, toluene, xylene, chlorobenzene and dichlorobenzene), nitriles (acetonitrile), ethers (dibutyl ether, dioxane, tetrahydrofuran, ethylene glycol dimethyl ether or diethylene glycol dimethyl ether). Isolation and purification can be carried out by conventional methods, for example crystallization, distillation or chromatography.

Compounds of the formula II are known in part (see, for example, H. P. Cava et al., J. Am. Chem. Soc., p. 1701 (1957) and J. W. Barton et al., J. Chem. Soc. Perkin Trans. 1, p. 967–971 (1986)) or can be prepared by analogous processes. The substituted 1,2-bis(dichloro- or dibromomethyl)benzenes which are required for the preparation are also known in part or are available by conventional electrophilic or nucleophilic substitution reactions of the corresponding o-dimethylbenzenes, followed by their chlorination or bromination with, for example, N-chloro- or N-bromo-succinimide.

The p-naphthoquinones of the formula III are novel and available, for example, by nucleophilic substitution of protected or unprotected and substituted or unsubstituted 6-halo- or 6-nitro-1,4-naphthoquinones with $R^2SH$ in the presence of alkali metal compounds ($K_2CO_3$, $Cs_2CO_3$, KOH, NaOH, $NaNH_2$, $NaOCH_3$, $NaOC_2H_5$) or with $R^2SX^1$ in which $X^1$ is, for example, Li, K, Na, Rb or Cs. Halo- and nitronaphthoquinones have been described, for example, in Houber-Weyl, Quinones I, Volume 7/3b (1977). The naphthoquinones of the formula III can also be prepared in a known manner by electrophilic or nucleophilic substitution of substituted or unsubstituted naphthalenes, dihydro- or tetrahydronaphthalenes, followed by convertion to the substituted 1,4-naphthoquinones.

The compounds of the formula I can also be prepared by reacting 1,2-bis(dihalomethyl)benzenes of the formula

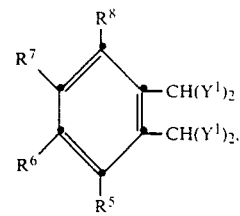

in which $Y^1$ is Cl, Br or I in the presence of NaI in an organic solvent with a compound of the formula III. This method has been described by J. W. McOmie in Synthesis, p. 416–417 (1973).

The compounds of the formula I can also be obtained by reacting 1,4-anthraquinones of the formula

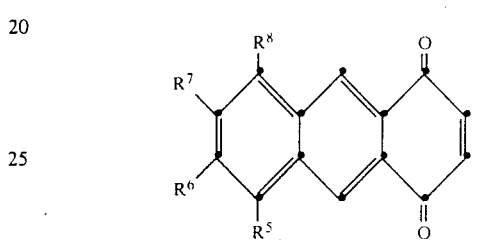

with an α-pyrone of the formula IV

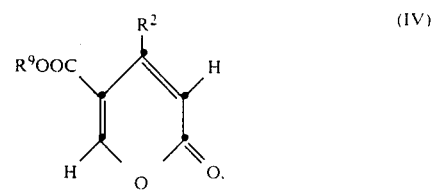

(IV)

or a butadiene of the Formel V

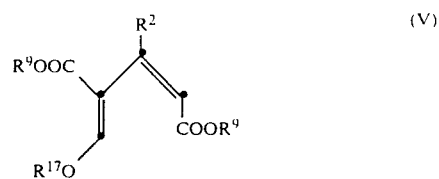

(V)

in which $R^{17}$ is $C_1$–$C_6$alkyl and $R^9$ is as defined above and preferably $C_1$–$C_6$alkyl. This method and the preparation of α-pyrones has been described in U.S. Pat. No. 4,617,151 and EP-A No. 0,195,743.

The compounds of the formula IV and V are available, for example, as follows:

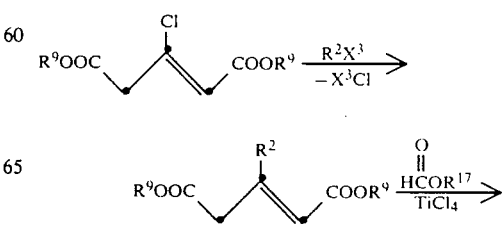

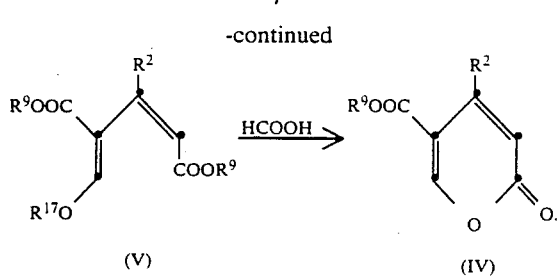

(V)　　　　　　　　(IV)

The compounds of the formula I can also be obtained in a known manner by cyclizing substituted or unsubstituted naphthalenedicarboxylic anhydrides of the formula

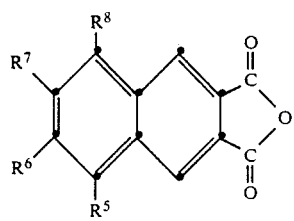

according to Friedel-Crafts with a benzene of the formula

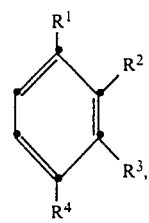

in the presence of a Lewis acid.

By means of the processes described, it is also possible to prepare naphthacene-5,12-diones containing nucleophilically substitutable groups (for example —$NO_2$, F, Cl, Br) in the 1-, 2-, 3-, 4-, 7-, 8-, 9- and/or 10-positions, in which other nucleophilic groups $R^1$ to $R^8$ and $R^{16}S$— can be introduced by nucleophilic substitution. Where $R^{16}$ is a polyoxaalkylene radical, this type of compound can also be obtained by reaction of the compounds of the formula I where $R^{16}$ is hydroxyalkyl with epoxides. Furthermore, it is possible to modify the radicals $R^1$ to $R^8$ by classic reactions, for example hydrolysis, esterification or trans-esterification, amidation, oxidation or reduction.

The compounds of the formula I are in general crystalline and are distinguished by high thermal stability. The compounds are highly soluble in curable compositions, if necessary together with a solvent.

They are highly suitable either by themselves or together with H donors such as tertiary amines, alcohols or phenylacetic acid derivatives as very effective photoinitiators or sensitizers for light-induced polymerization or dimerization of ethylenically unsaturated compounds. In these reactions, their are distinguished by high light sensitivity and activity over a wavelength range of about 200 nm (UV light) to about 600 nm. The properties of the compounds according to the invention, for example solubility, melting point and absorption range can be selectively influenced by the choice of substituents.

The present invention further relates to a composition polymerizable by irradiation, containing (a) at least one nonvolatile monomeric, oligomeric or polymeric compound having at least one polymerizable or dimerizable ethylenically unsaturated double bond and (b) at least one compound of the formula I as photoinitiator or sensitizer.

The compositions can contain further photoinitiators or sensitizers which are different from (b).

The amount of compounds according to the invention to be added depends for the most part on economic aspects, their solubilities and the sensitivity required. In general, 0.01 to 20, preferably 0.05-10, and particularly 0.1 to 5, % by weight are used, relative to component (a).

Suitable components (a) are those ethylenically unsaturated monomeric, oligomeric and polymeric compounds which react by photopolymerization to give high-molecular-weight products, thus changing their solubility.

Particularly suitable compounds are, for example, esters of ethylenically unsaturated carboxylic acids and polyols or polyepoxides and polymers having ethylenically unsaturated groups in the chain or in the side groups, for example unsaturated polyesters, polyamides and polyurethanes and copolymers thereof, polybutadiene and butadiene copolymers, polyisoprene and isoprene copolymers, polymers and copolymers having (meth)acrylic groups in side chains, and also mixtures of one or more of these polymers.

Examples of unsaturated carboxylic acids are acrylic acid, methacrylic acid, crotonic acid, itaconic acid, cinnamic acid, unsaturated fatty acids such as linolenic acid or oleic acid. Acrylic and methacrylic acid are preferred.

Suitable polyols are aromatic and in particular aliphatic and cycloaliphatic polyols. Examples of aromatic polyols are hydroquinone, 4,4'-dihydroxydiphenyl, 2,2-di(4-hydroxyphenyl)propane, and also novolaks and resols. Examples of polyepoxides are those based on the polyols mentioned, in particular the aromatic polyols and epichlorohydrin. Furthermore, polymers or copolymers which contain hydroxyl groups in the polymer chain or in side groups, for example polyvinyl alcohol and copolymers thereof or hydroxyalkyl polymethacrylates or copolymers thereof, are also suitable as polyols. Further suitable polyols are oligo esters containing terminal hydroxyl groups.

Examples of aliphatic and cycloaliphatic polyols are alkylene diols preferably having 2 to 12 C atoms, such as ethylene glycol, 1,2- or 1,3-propanediol, 1,2-, 1,3- or 1,4-butanediol, pentanediol, hexanediol, octanediol, dodecanediol, diethylene glycol, triethylene glycol, polyethylene glycols having molecular weights of preferably 200 to 1,500, 1,3-cyclopentanediol, 1,2-, 1,3- or 1,4-cyclohexanediol, 1,4-dihydroxymethylcyclohexane, glycerol, tris($\beta$-hydroxyethyl)amine, trimethylolethane, trimethylolpropane, pentaerythritol, dipentaerythritol and sorbitol.

The polyols can be partially or completely esterified with one or different unsaturated carboxylic acids, in which the free hydroxyl groups in the partial esters can be modified, for example etherified or esterified with other carboxylic acids.

Examples of esters are: trimethylolpropane triacrylate, trimethylolethane triacrylate, trimethylolpropane trimethacrylate, trimethylolethane trimethacrylate, tetramethylene glycol dimethacrylate, triethylene glycol dimethacrylate, tetraethylene glycol diacrylate, pentaerythritol diacrylate, pentaerythritol triacrylate, pentaerythritol tetraacrylate, dipentaerythritol diacrylate, dipentaerythritol triacrylate, dipentaerythritol tetraacrylate, dipentaerythritol pentaacrylate, dipentaerythritol hexaacrylate, tripentaerythritol octaacrylate, pentaerythritol dimethacrylate, pentaerythritol trimethacrylate, dipentaerythritol dimethacrylate, dipentaerythritol tetramethacrylate, tripentaerythritol octamethacrylate, pentaerythritol diitaconate, dipentaerythritol trisitaconate, dipentaerythritol pentaitaconate, dipentaerythritol hexaitaconate, ethylene glycol dimethacrylate, 1,3-butanediol diacrylate, 1,3-butanediol dimethacrylate, 1,4-butanediol diitaconate, sorbitol triacrylate, sorbitol tetraacrylate, pentaerythritol (modified) triacrylate, sorbitol tetramethacrylate, sorbitol pentaacrylate, sorbitol hexaacrylate, oligoester acrylates and oligoester methacrylates, glycerol diacrylate and triacrylate, 1,4-cyclohexane diacrylate, bisacrylates and bismethacrylates of polyethylene glycol having molecular weights of 200-1,500, or mixtures thereof.

Suitable components (a) are also the amides of identical or different unsaturated carboxylic acids of aromatic, cycloaliphatic and aliphatic polyamines preferably having 2 to 6, particularly 2 to 4, amino groups. Examples of these polyamines are ethylene diamine, 1,2- or 1,3-propylenediamine, 1,2-, 1,3- or 1,4-butylenediamine, 1,5-pentylenediamine, 1,6-hexylenediamine, octylenediamine, dodecylenediamine, 1,4-diaminecyclohexane, isophoronediamine, phenylenediamine, bisphenylenediamine, di-$\beta$-aminoethyl ether, diethylenetriamine, triethylenetetramine, di($\beta$-aminoethoxy)ethane or di($\beta$-aminopropoxy)ethane. Further suitable polyamines are polymers and copolymers having amino groups in the side chain and oligoamides having terminal amino groups.

Examples of these unsaturated amides are: methylenebisacrylamide, 1,6-hexamethylenebisacrylamide, diethylenetriaminetrismethacrylamide, bis(methacrylamidopropoxy)ethane, $\beta$-methacrylamidoethylmethacrylate, N[($\beta$-hydroxyethoxy)ethyl]acrylamide.

Suitable unsaturated polyesters and polyamides are derived, for example, from maleic acid and diols or diamines. Maleic acid can be replaced in part by other dicarboxylic acids. They can be used together with ethylenically unsaturated comonomers, for example styrene. The polyesters and polyamides can also be derived from dicarboxylic acids and ethylenically unsaturated diols or diamines, in particular from those having longer chains of, for example, 6 to 20 C atoms. Examples of polyurethanes are those synthesized from saturated or unsaturated diisocyanates and unsaturated and saturated diols.

Polybutadiene and polyisoprene and copolymers thereof are known. Examples of suitable comonomers are polyolefins such as ethylene, propene, butene, hexene, (meth)acrylates, acrylonitrile, styrene or vinyl chloride. Polymers having (meth)acrylate groups in the side chain are also known. They can be, for example, reaction products of epoxy resins based on novolaks with (meth)acrylic acid, homopolymers or copolymers of polyvinyl alcohol or hydroxyalkyl derivatives thereof, which are esterified with (meth)acrylic acid, or they are homopolymers and copolymers of hydroxyalkyl esters of (meth)acrylic acid.

The photopolymerizable compounds can be used by themselves or in any desired mixture. Mixtures of polyol (meth)acrylates are preferably used. Suitable dimerizable compounds are those containing, for example, cinnamic acid radicals, 3,4-substituted maleimidyl radicals or

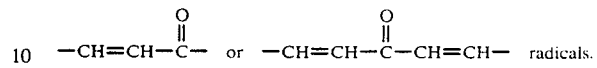

These radicals are in general bound to oligomers or polymers, for example in the polymer chain or as side groups. Polymers containing maleimidyl groups have been described, for example, in DE-A No. 2,626,795. The maleimidyl group can conform to the formula

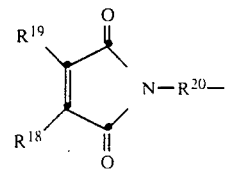

in which $R^{18}$ and $R^{19}$ are $C_1$-$C_{12}$alkyl, $C_5$cycloalkyl or $C_6$cycloalkyl, $C_6$-$C_{12}$aryl, halogen (for example Cl or Br), or $R^{18}$ and $R^{19}$ together are trimethylene or tetramethylene, and $R^{20}$ is a bridging group, for example $C_2$-$C_{12}$alkylene or phenylene. Epoxy resins containing

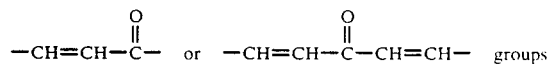

have been described, for example, in DE-A No. 2,342,407.

It is also possible to add binders to the compositions according to the invention, which is particularly advantageous in the case where the photopolymerizable or photodimerizable compounds are liquid or viscous substances. The amount of binder can be, for example, 5-95, preferably 10-90, and particularly 50-90, % by weight, relative to the entire composition. The choice of binder depends on the area of application and properties required, such as developability in aqueous and organic solvent systems, adhesion on substrates and sensitivity to oxygen.

Examples of suitable binders are polymers having a molecular weight of about 5,000-2,000,000, preferably 10,000 to 1,000,000. Examples are: acrylate and methacrylate homopolymers and copolymers, for example copolymers of methyl methacrylate/ethyl acrylate/methacrylic acid, poly(alkyl methacrylate), poly(alkyl acrylate); cellulose esters and cellulose ethers such as cellulose acetate, cellulose acetobutyrate, methylcellulose, ethylcellulose; polyvinylbutyral, polyvinylformal, cyclized rubber, polyethers such as polyethylene oxide, polypropylene oxide, polytetrahydrofuran; polystyrene, polycarbonate, polyurethane, chlorinated polyolefins, polyvinyl chloride, copolymers of vinyl chloride/vinylidene chloride, copolymers of vinylidene chloride with acrylonitrile, methyl methacrylate and vinyl acetate, polyvinyl acetate, copoly(ethylene/vinyl acetate), polyamides such as polycaprolactam and poly(hexamethylenedipamide), polyesters such as poly(ethylene glycol terephthalate) and poly(hexamethylene glycol succinate).

The compositions according to the invention are suitable as coating agents for substrates of many types, for example wood, paper, ceramics, plastics, such as polyesters and cellulose acetate films, and metals such as copper and aluminium onto which a protective film or a photographic image is to be applied by photopolymerization. The present invention furthermore relates to the coated substrates and to a process for the application of photographic images to the substrates. The coated substrates can also be used as recording material for holograms (volume phase diagram), it being advantageous that no wet development is necessary for this purpose.

The coating of the substrates can be carried out by applying a liquid composition, a solution or suspension, to the substrate. Liquid compositions without solvent are preferred.

The choice of solvent and the concentration depends mainly on the type of composition and the coating process. The composition is applied uniformly to a substrate by means of known coating processes, for example by dip-coating, knife-coating, curtain-coating, electrophoresis, brush-coating, spray-coating or reverse-roll-coating. The amount applied (film thickness) and type of substrate (film support) depend on the desired area of application. Examples of film supports for recording photographic information are polyester or cellulose acetate films or papers coated with plastics; for offset printing forms specially treated aluminium and for the production of printed circuits copper laminates. The film thicknesses for photographic materials and offset printing forms are in general about 0.5 to about 10 μm; for printed circuits in general 1 to about 100 μm. Any solvents used are removed after coating.

Photocurable compositions, such as are used for a variety of purposes, contain in most cases, in addition to the photopolymerizable compounds and the photoinitiators, a number of other additives. Thus, it is often customary to add thermal inhibitors, which are intended to protect against premature polymerization in particular during the preparation of the compositions, which is effected by mixing the components. For this purpose, for example, hydroquinone, hydroquinone derivatives, p-methoxyphenol, β-naphthols or sterically hindered phenols, for example 2,6-di(tert-butyl)-p-cresol, are used. Furthermore, small amounts of UV absorbers can be added, for example those of the benzotriazole, benzophenone or oxalanilide type. Light stabilizers of the type of sterically hindered amines (HALS) can also be added.

To increase the storage stability in the dark, copper compounds such as copper naphthenate, copper stearate or copper octanoate, phosphorus compounds such as triphenylphosphine, tributylphosphine, triethyl phosphite, triphenyl phosphite or tribenzyl phosphite, quaternary ammonium compounds such as tetramethylammonium chloride or trimethylbenzylammonium chloride or hydroxylamine derivatives, for example N-diethylhydroxylamine, can be added.

To exclude the inhibiting effect of atmospheric oxygen, paraffin or similar wax-like substances are often added to photocurable mixtures. At the start of the polymerization, these float out as a result of insufficient solubility in the polymer and form a transparent surface layer, which keeps out the air.

Further customary additives are photosensitizers which absorb at certain wavelengths and pass on the absorbed energy to the initiators or themselves function as additional initiator. Examples of these are in particular thioxanthone, anthracene, anthraquinone and coumarin derivatives.

Further customary additives are accelerators of the amine type, which are of importance in particular in pigmented formulations, since they act as chain transfer agents. Examples of these are N-methyldiethanolamine, triethylamine, ethyl p-dimethylaminobenzoate or Michler's ketone. The effect of the amines can be reinforced by the addition of aromatic ketones of the benzophenone type.

Further customary additives are, for example, fillers, pigments, dyes, adhesion promoters, wetting agents and flow-improving agents.

Photocuring is of great importance for printing inks, since the drying time of the binder is a decisive factor for the production rate of graphic products and should be of the order of fractions of seconds. UV-curable printing inks are of particular importance for screen printing.

The photocurable compositions according to the invention are also very suitable for the preparation of printing plates, especially flexographic printing plates. For this purpose, for example, mixtures of soluble linear polyamides or of styrene/butadiene rubber with photopolymerizable monomers, for example acrylamides or acrylates, and a photoinitiator are used. Films and plates made from these systems are exposed through the negative (or positive) of the original, and the uncured components are then eluted by means of a solvent.

A further area of application of photocuring is metal coating, for example in the coating of metal sheets for tubes, cans or bottle closures, and the photocuring of plastic coatings, for example floor and wall coverings based on PVC.

Examples of photocuring of paper coatings are the colourless coating of labels, grammophone record jackets or book jackets.

The use of photocurable compositions for imaging processes and for the optical production of information carriers is also important. In these processes, the film applied to the carrier (wet or dry) is exposed through a photomask to light of short wavelength, and the unexposed areas of the film are removed by treatment with a solvent (=developer). The exposed areas are crosslinked polymers and are therefore insoluble and remain on the carrier. When coloured appropriately, visible images are formed. In a carrier consisting of a metallized film, the metal can after exposure and development be etched away at the unexposed areas or reinforced by galvanization. In this manner, it is possible to produce printed circuits.

Light soures which are suitable for exposure are those having a high percentage of light of short wavelength. Nowadays suitable technical installations and various types of lamps are available for this. Examples are carbon-arc lamps, xenon-arc lamps, mercury vapour lamps, metal-halogen lamps, fluorescent lamps, argon lamps or photographic floodlight lamps. As of late, laser light sources are also being used. These have the advantage of not requiring photomasks; the directed laser beam writes directly on the photocurable film.

Accordingly, the invention further relates to
(a) a coated substrate which is coated on at least one surface by a composition according to the invention;
(b) a process for the photographic production of relief images or coatings, which comprises subjecting a coated substrate to imagewise or uniform exposure and removing unexposed portions afterwards with a solvent;

(c) the use of compounds of the formula I as initiators and sensitizers for the photopolymerization or photodimerization of nonvolatile monomeric, oligomeric or polymeric compounds having at least one polymerizable or dimerizable ethylenically unsaturated double bond; and (d) the use of a composition according to the invention for the preparation of coatings, printing inks, printing plates, resist materials and also as image recording material and coating agent.

The photoinitiators according to the invention can also be used in the preparation of polymers, for example for flocculants or articles for hygiene (see, for example, EP-A No. 0,031,005 and DE-A No. 2,545,290).

The compounds of the formula I are valuable intermediates for the preparation of substituted tetrathiotetracenes and tetraselenotetracenes (cf. U.S. Pat. No. 4,617,151). This type of chalcogenated tetracene can be used to prepare electrically conducting charge-transfer complexes (CT complexes), with electron acceptors. They can be bound to polymers, for example incorporated as side groups into polymers (cf. U.S. Pat. No. 4,617,151), by means of their functional substituents. The CT complexes are also suitable for the preparation, for example, of antistatic coatings of photographic film elements, magnetic tapes, electrophotographic film elements and electronic components (see U.S. Pat. No. 3,634,336). Furthermore, the chalcogenated tetracenes have electrochromic properties; they can be used for electrochromic displays. They are also suitable as laser-optical data storage units [Nach. Chem. Techn. Lab. 35, p. 255 ff (1987)] and as anode material in organic solid state batteries (EP-A No. 0,090,598). CT complexes of substituted tetrathiotetracenes or tetraselenotetracenes can also be incorporated into thermoplastic, thermosetting or elastomeric polymers to achieve antistatic properties. This is advantageously done, for example, by dissolving the substituted tetrathiotetracenes or tetraselenotetracenes together with a soluble polymer or a precursor thereof and an electron acceptor, for example a halogen-forming agent (organic halogenated compounds, for example bromoform, trichlorobromomethane, tetrabromomethane, hexachloropropane, perchlorobutadiene, 1,3- or 1,4-dichloro-2-butene, 1,4-bis(trichloromethyl)benzene, iodoacetonitrile, iodoform, tetrachloroethylene, perchlorocyclobutadiene, N-chloro-, N-bromo- or N-iodosuccinimid) if appropriate together with a further inert solvent, and evaporating the excess halogen-forming agent and the solvent at elevated temperature. The composition formed contains in the polymer a network of needle-like crystals of the CT complex, provided that the chalcogenated tetracene is unsubstituted or contains small substituents (e.g. F, $CH_3$, $CF_3$). This type of composition has a high electric conductivity. This conductivity can be improved even further by also using a substituted tetrathiotetracene or tetraselenotetracene prepared from the compounds of the formula I and which does not form such a network and is present in the polymer matrix in finely divided form, since these substituted tetrathiotetracenes or tetraselenotetracenes have no or only a small tendency to crystallize in the polymer. Furthermore, naphthacenequinones can also be used in electrochromic display elements (Japanese Preliminary Published Application No. 61-43680).

The examples which follow illustrate the invention.

Examples 1-12

2-(2-Hydroxyethylthio)naphthacene-5,12-dione 1 g (3.62 mmol) of 2-fluoronaphthacene-5,12-dione (prepared according to U.S. Pat. No. 4,522,754), 0.31 g (3.98 mmol) of 2-mercaptoethanol, 1.50 g (10.86 mmol) of potassium carbonate and 10 ml of DMSO are stirred at 25° C. for 3 minutes. The mixture is poured into water. The crystals are filtered off and dissolved in tetrahydrofuran/toluene, the solution dried over sodium sulfate and evaporated. The residue is recrystallized from THF/toluene/pentane. Yield 1 g (83%); melting point 195°-196° C.

The compounds listed in Table 1 below are prepared analogously:

TABLE 1

| Example | R | Reaction time (minutes) | Yield (%) | Melting point (°C.) |
|---|---|---|---|---|
| 2 | —$CH_3$* | 10 | 87 | 225-28 |
| 3 | —$CH_2$—$CH_3$ | 120 | 93 | 179-81 |
| 4 | —$(CH_2)_{11}$—$CH_3$ | 20 | 81 | 130-34 |
| 5 | —$CH_2$—$CH_2$—COO—$CH_2$CH($CH_2CH_3$)$CH_2CH_2CH_2CH_3$ | 10 | 88 | 100-103 |
| 6 | —$CH_2$—COO—$CH_2$CH($CH_2CH_3$)$CH_2CH_2CH_2CH_3$ | 10 | 50 | 82-84 |
| 7 | —$CH_2$—$COOCH_3$ | 180 | 51 | 129-30 |
| 8 | —$CH_2$—$CH_2$—$NH_2$ | 50 | 86 | 155-60 |
| 9 | —$CH_2$—CH(OH)—$CH_2$—OH | 45 | 93 | 140-41 |

TABLE 1-continued

[Structure: naphthacene-5,12-dione with S—R substituent]

| Example | R | Reaction time (minutes) | Yield (%) | Melting point (°C.) |
|---------|---|------------------------|-----------|---------------------|
| 10 | —CH₂—⌬ (benzyl) | 10 | 85 | 200–203 |
| 11 | ⌬ (phenyl) | 120 | 75 | 207–10 |
| 12 | ⌬—CH₃ (tolyl) | 10 | 87 | 200–203 |

*In this example, NaSCH₃ is used instead of the mercaptan.

Example 13

2,8- and 2,9-Bis(2-hydroxyethylthio)naphthacene-5,12-dione 2 g (6.8 mmol) of a mixture of 2,8- and 2,9-difluoronaphthacene-5,12-dione are stirred at 80° C. for 6.5 hours with 3.76 g (27.2 mmol) of potassium carbonate, 1 g (20.4 mmol) of 2-mercaptoethanol and 25 ml of acetonitrile. The mixture is poured into dilute hydrochloric acid. The precipitate is filtered off, washed three times with water, then dried and recrystallized from o-dichlorobenzene; yield 2.64 g (95%) of orange crystals of melting point 180°–190° C.

The 2,8-/2,9-difluoronaphthacene-5,12-dione mixture is prepared as follows: a mixture of 12.9 g (0.06 mol) of 6-fluoronaphthalene-2,3-dicarboxylic anhydride, 20.1 g of AlCl₃ and 450 ml of fluorobenzene is heated to reflux with stirring for one hour. After cooling, the reaction mixture is poured onto a mixture of ice and 15 ml of concentrated HCl. The organic phase is separated off and evaporated to dryness in vacuo. The residue is partitioned between CHCl₃ and NaHCO₃ solution, the aqueous phase is treated with carbon and acidified with concentrated HCl until it is acid to Congo red. The precipitate formed is filtered off and dried. This gives 13.1 g (72%) of a 1:1 mixture of 6- and 7-fluoro-3-(4-fluorobenzoyl)-2-naphthalenecarboxylic acid of melting point 251°–253° C.

This mixture is added in portions with stirring over a period of 30 minutes at 145° C. to a melt of 124.3 g of AlCl₃ and 28 g of NaCl. The melt is stirred for 3.5 hours and then poured onto ice. The precipitate formed is filtered off and dried. The crude product (22 g) obtained is extracted in a Soxhlet apparatus with CHCl₃ for 20 hours. After cooling, 4 g of product crystallize out. The mother liquor is washed with 1N NaOH and H₂O, and the solvent is then evaporated. This gives another 3 g of product, which is purified by sublimation in a high vacuum at 230° C. Yield: 6.3 g (47%), melting point 275°–277° C., mass spectrum: M⁺ 294/100.

Using the same procedure and naphthalene-2,3-dicarboxylic anhydride and 1,2-difluorobenzene gives 2,3-difluoronaphthacene-5,12-dione.

Example 14

3-Fluoro-2-methylthionaphthacene-5,12-dione 1 g (3.4 mmol) of 2,3-difluoronaphthacene-5,12-dione, 0.94 g (6.8 mmol) of potassium carbonate, 0.47 g (6.8 mmol) of sodium methanethiolate and 20 ml of tetrahydrofuran are stirred at 25° C. for 2.5 hours. The mixture is poured into dilute hydrochloric acid and extracted with THF/toluene. The organic phase is dried over sodium sulfate and evaporated. The residue is chromatographed on silica gel with toluene. Yield 0.55 g (50%); melting point 230°–235° C.

Example 15

2,3-Bis(methylthio)naphthacene-5,12-dione 1 g (3.4 mmol) of 2,3-difluoronaphthacene-5,12-dione, 0.94 g (6.8 mmol) of potassium carbonate, 0.72 g (10.2 mmol) of sodium methanethiolate and 20 ml of THF are stirred under reflux for 4 hours. The mixture is poured into dilute hydrochloric acid. The precipitate is filtered off, washed with water and dried at 140° C. in vacuo. Recrystallization from dioxane gives 1 g (84%) of pure product, melting point >260° C.

Example 16

2,3-Bis(2′-ethylhexyloxycarbonylmethylthio)naphthacene-5,12-dione 1 g (3.4 mmol) of 2,3-difluoronaphthacene-5,12-dione, 0.94 g (6.8 mmol) of potassium carbonate, 2.0 g (10.2 mmol) of 2-ethylhexyl thioglycolate and 10 ml of THF are stirred at 65° C. for 20 hours. The mixture is taken up in water/THF/toluene. The organic phase is washed with dilute hydrochloric acid, then twice with water, dried over sodium sulfate, and evaporated. Recrystallization from diethyl ether/pentane gives 2.04 g (91%) of product. Melting point 75°–80° C.

Examples 17–20

Analogously to Example 1, using 9-fluoronaphthacene-5,12-dione and the corresponding mercaptans gives 9-methyl-(17), 9-ethyl-(18), 9-phenyl-(19) and 9-(2'-hydroxyethyl)naphthacene-5,12-dione (20).

Examples 21 and 22

According to Example 1, 2,3-di(trifluoromethyl)-8,9-dibromonaphthacene-5,12-dione and 8,9-dibromonaphthacene-5,12-dione are reacted with thiophenol. This gives 2,3-di(trifluoromethyl)-8,9-di(phenylthio)naphthacene (yield: 65%; melting point >260° C.) and 8,9-di(phenylthio)naphthacene (yield: 88%, melting point >260° C.).

(B) Use Examples

Example 23

Photocuring of an acrylate mixture for the preparation of a relief image

A photocurable composition is prepared by mixing the following components:

|  | Solids content |
| --- | --- |
| 150.30 g of Scripset 540[(1)] (30% solution in acetone) | 45.1 g |
| 48.30 g of trimethylolpropane triacrylate | 48.3 g |
| 6.60 g of polyethylene glycol diacrylate | 6.6 g |
| 0.08 g of crystal violet |  |
| 205.28 g | 100.0 g |

[(1)]Polystyrene/maleic monoester copolymer (Monsanto)

Portions of this composition are mixed with 0.2% (relative to the composition) of the photoinitiators listed in the table below. All operations are carried out under red light or yellow light.

The samples to which initiator has been added are applied to 200 μm aluminium foil (10×15 cm) by means of a 150 μm wire-wound draw bar. The solvent is removed in a through-circulation oven by heating to 60° C. for 15 minutes. This results in a dry film thickness of 35 μm. On this film is placed a 76 μm thick polyester sheet and on top of that a standardized test negative containing 21 steps of various optical densities (Stouffer wedge). A second polyester sheet is placed on top of that, and the laminate thus obtained is fixed on a metal sheet by means of vacuum. The sample is then exposed at a distance of 30 cm by means of a 5 kW metal halide lamp (type MO 23), which is done for 20 seconds in a first test series and for 40 seconds in a second test series. After exposure, the sheets and the mask are removed, the exposed film is developed in an ultrasonic bath by means of developer A for 2 minutes and subsequently dried in a through-circulation oven at 60° C. for 15 minutes. The sensitivity of the initiator system used is characterized by the number of the last wedge step which has been reproduced adhesion-free. The higher the number of steps, the more sensitive the system. An increase by two steps means approximately a doubling of the curing rate. The results are shown in Table 2. Developer A contains 15 g of sodium metasilicate×9-H₂O; 0.16 g of KOH; 3 g of polyethylene glycol 6000; 0.5 g of levulinic acid and 1,000 g of deionized water.

TABLE 2

| Photoinitiator | Number of steps reproduced | |
| --- | --- | --- |
| Naphthacenedione from Example | after 20 s | after 40 s of exposure |
| 1 | 10 | 12 |
| 2 | 10 | 12 |
| 3 | 9 | 11 |
| 4 | 8 | 10 |
| 5 | 6 | 8 |
| 6 | 7 | 9 |
| 7 | 7 | 9 |
| 9 | 9 | 11 |
| 10 | 1 | 4 |
| 11 | 4 | 5 |
| 16 | 8 | 10 |
| 17 | 6 | 9 |
| 18 | 5 | 7 |
| 19 | 4 | 6 |
| 20 | 7 | 9 |

Example 24

A solution of the composition:

| Ethylcellosolve | 71.00 g |
| --- | --- |
| Scripset 550* | 14.00 g |
| Trimethylolpropane triacrylate | 15.00 g |
| Polyethylene glycol 200 diacrylate | 2.00 g |

*Styrene/maleic monoester copolymer ($M_w$ = 10'000, acid number 190), manufactured by Monsanto is divided into equal portions of 10 grams each. In this solution, 0.05 g of naphthacenedione and 0.5 g of glycerol are in each case dissolved under red light.

Coatings having a wet film thickness of 12 micrometers are applied to a transparent polyester sheet by means of a wire-wound draw bar. The wet films are dried in a through-circulation oven at 80° C. for 30 minutes.

By dipping the films into a solution of

| Mowiol 4-88 (polyvinyl alcohol) | 30.00 g |
| --- | --- |
| Brij 35 (10% in water)** | 15.00 g |
| Deionized water | 250.00 g |

** Polyoxyethylene lauryl ether (wetting agent, manufactured by Atlas Powder)

and subsequent drying at 80° C. in a through-circulation oven, an oxygen barrier film 0.5 micrometer thick is applied.

The dry film is exposed to a 5,000 W mercury lamp (MO 33, from Staub, Neu-Isenburg) through a step wedge at increments of 0.15 (log O.D.) and subsequently developed to a relief image in a solution of the composition

| Sodium metasilicate nonahydrate | 15.00 g |
| --- | --- |
| Strontium hydroxide octahydrate | 0.30 g |
| Polyglycol 6000 | 3.00 g |
| Levulinic acid | 0.50 g |
| Deionized water | 1,000.00 g |

The light intensity is measured by means of a power meter from Oriel which contains a 365 nm sensor. Table 3 shows the light energy required for reaching step 7 of the step wedge.

TABLE 3

| Naphthacenedione | UV spectrum (extinction at $\lambda_{max}$) | $WP_7$ (mJ/cm$^{-2}$) |
|---|---|---|
| 2-Phenylthio-naphtha-cene-5,12-dione | $\epsilon = 11600$, $\lambda_{max}$: 398 nm shoulder at 418 nm | 26.4 |
| 2-Ethylthio-naphthacene-5,12-dione | $\epsilon = 10560$, $\lambda_{max}$: 398 nm shoulder at 418 nm | 660 |

Example 25

Manufacture of a negative offset printing plate

A coating solution of

| | |
|---|---|
| DMI polymer[1], 40% in methoxypropanol | 2.5 g |
| Naphthacene-5,12-dione, 1% in dimethylformamide | 5.0 ml |
| Rhodamine B (dye), 1% in ethylcellosolve | 0.5 ml |
| Ethylglycol acetate | 2.5 ml |

[1]Copolymer of 86 parts by weight of 1-(dimethylmaleimidyl)-6-meth-acroyloxy-n-hexane and 14 parts by weight of methacrylic acid, $M_w$ = 120,000 (determined by GPC, polystyrene standard)

is applied by means of centrifugal coating (30 sec. at 500 rpm) to an offset plate substrate, that is to say, an electrolytically roughened and anodized aluminium sheet and dried at 80° C. for 15 minutes. This gives a coating weight of 1.1–1.3 g/m². It is then exposed to a 2,000 watt metal halogen lamp for 100 seconds (distance 75 cm from the frame of the vacuum chamber) through a Stouffer wedge (increments of the optical density O.D.=0.15). The development is carried out manually at 20° C. by gentle rubbing for 45 seconds with a tampon soaked with the following developer solution:

| | |
|---|---|
| 75.0 g of sodium metasilicate pentahydrate | |
| 0.4 g of wetting agent (Supronic B 50, ABM Chemicals Ltd.) | |
| 925.0 g of deionized water. | |

In Table 4, the naphthacenediones used and the last visible step are shown

TABLE 4

| Naphthacene-5,12-dione from example | Last visible step |
|---|---|
| 1 | 7 |
| 3 | 7 |
| 5 | 7 |
| 8 | 7 |
| 11 | 8–9 |

The crosslinked portions of the image have high abrasion resistance and allow the production of a large number of copies.

Example 26

Sensitization of the 2+2 cycloaddition

5% (w/w) 2-phenylthionaphthacene-5,12-dione are dissolved in a 20% (w/w) solution of a copolymer of molecular weight 140,000 dalton (measured by light scattering in dioxane at 25° C.) from 20 mol-% of ethyl acrylate and 80 mol-% of N-(5-methyl-3-oxa-4-oxohex-en-5-yl)dimethylmaleimide (prepared by the process in Angew. Makromol. Chem. 115 (1983) 163 ff and Angew. Makromol. Chem. 128 (1984) 71 ff). The solution is applied as a film to a copper-coated glass fibre/epoxide laminate in a wet film thickness of 14 μm by means of a wire-wound draw bar, and the film is dried at 80° C. for 1 hour. The dry film is exposed to a 5,000 W mercury lamp (MO 33 from Staub, Neu-Isenburg) through a step wedge at increments of 0.15 (log O.D.) and subsequently developed in 1,1,1-trichloroethane to a relief image. The light intensity $WP_7$ determined according to Example 18 is 165 mJ/cm$^{-2}$.

What is claimed is:

1. A compound of the formula I

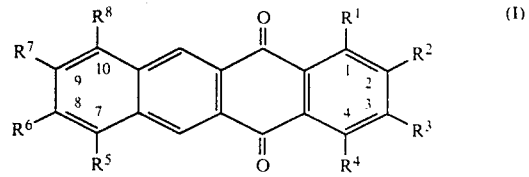

in which $R^1$, $R^2$, $R^3$, $R^4$, $R^5$, $R^6$, $R^7$ and $R^8$, independently of one another, are H, —CN, —NO$_2$, halogen, —NR$^{10}$R$^{11}$, COOR$^9$, —CONR$^{10}$R$^{11}$, —SiR$^{13}$R$^{14}$R$^{15}$, or R$^1$–R$^8$ are C$_1$–C$_{20}$alkyl-(X)$_p$—, C$_2$–C$_{20}$alkenyl-(X)$_p$—, C$_2$–C$_{18}$alkynyl-(X)$_p$—, C$_3$–C$_8$cycloalkyl-(X)$_p$—, C$_6$–C$_{12}$aryl-(X)$_p$— or C$_7$–C$_{14}$aralkyl-(X)$_p$— or —Y—(C$_m$H$_{2m}$—O)-$_n$—R$^{12}$ which is unsubstituted or substituted by OH, —CN, —NR$^{10}$R$^{11}$, halogen, C$_1$–C$_{18}$alkyl, -alkoxy, alkylthio-, —COOR$^9$ or —CONR$^{10}$R$^{11}$;

X is O, S, SO or SO$_2$ and p is 0 or 1; Y is O or S; $R^9$ is H or the radical minus a hydroxyl hydrogen atom of a C$_1$–C$_{20}$alcohol and R$^{10}$ and R$^{11}$, independently of one another, are H, C$_1$–C$_{18}$alkyl, phenyl, benzyl, cyclopentyl, cyclohexyl, C$_2$–C$_{12}$mono- or C$_{2-12}$dihydroxyalkyl, —(C$_m$H$_{2m}$—O)$_n$—R$^{12}$ or R$^{10}$ and R$^{11}$ together are tetra- or pentamethylene or 3-oxa-1,5-pentylene; m is 2 to 6, n is 2 to 20; R$^{12}$ is H or C$_1$–C$_{12}$alkyl; R$^{13}$, R$^{14}$ and R$^{15}$, independently of one another are C$_1$–C$_{12}$alkyl; at least one of the radicals R$^2$, R$^3$, R$^5$, R$^6$, R$^7$ and R$^8$ being a thio radical.

2. A compound according to claim 1, in which R$^1$ is H, —CF$_3$, —OH, C$_1$–C$_8$alkyl, unsubstituted or —OH—substituted C$_1$–C$_{18}$alkoxy, unsubstituted or halogen-, C$_1$–C$_6$alkyl- or C$_1$–C$_6$alkoxy-substituted C$_6$–C$_{10}$aryloxy, C$_7$–C$_{10}$aralkyloxy or —COOR$^9$ where R$^9$ is a C$_1$–C$_{20}$alcohol minus a hydroxyl hydrogen atom.

3. A compound according to claim 1, in which R$^4$, R$^5$ and R$^6$ are H.

4. A compound according to claim 1, in which R$^1$, R$^4$, R$^5$ and R$^8$ are H.

5. A compound according to claim 1, in which R$^2$ is a thio radical R$^{16}$—S-in which R$^{16}$ is unsubstituted or substituted C$_1$–C$_{20}$alkyl, cyclopentyl, cyclohexyl, phenyl or benzyl or is (C$_m$H$_{2m}$O)$_n$R$^{12}$, m being a number from 2 to 4, n a number from 2 to 12 and R$^{12}$ is H or C$_1$–C$_{12}$alkyl.

6. A compound according to claim 1, in which R$^1$ and R$^3$ to R$^8$, independently of one another, are H, —CN, —NO$_2$, —F, —Cl, —Br, —COOR$^9$, —NR$^{10}$R$^{11}$, —CONR$^{10}$R$^{11}$ in which R$^9$ is H or C$_1$–C$_{12}$alkyl and R$^{10}$ and R$^{11}$, independently of one another are H, C$_1$–C$_{12}$alkyl, —CH$_2$CH$_2$OH, —CH$_2$CH(OH)CH$_3$, —CH$_2$CHOHCH$_2$OH or (C$_m$H$_{2m}$O)$_n$R$^{12}$ where m is 2 or 3, n is a number from 2 to 12 and R$^{12}$ is H or C$_1$–C$_{12}$alkyl, or SiR$^{13}$R$^{14}$R$^{15}$ where R$^{13}$, R$^{14}$ and R$^{15}$ are C$_1$–C$_4$alkyl, or unsubstituted or substituted C$_1$–C$_{18}$alkyl(X)$_p$, C$_6$H$_5$(X)$_p$ or C$_6$H$_5$CH$_2$(X)$_p$ in which X is O or S and p is 0 or 1, or —Y(C$_m$H$_{2m}$O)$_n$R$^{12}$ in which Y is O or S, m is 2 or 3, n is a number from 2 to 12 and R$^{12}$ is H or C$_1$–C$_{12}$alkyl.

7. A compound according to claim 1, in which $R^3$, or $R^3$ and $R^6$ or $R^7$, or $R^3$, $R^6$ and $R^7$ are $R^{16}S-$ wherein $R_{16}$ is $C_1-C_{20}$alkyl, $C_2-C_{20}$alkenyl, $C_2-C_{20}$alkynyl, $C_3-C_8$cycloalkyl, $C_6-C_{12}$aryl, $C_7-C_{12}$aralkyl, or $-(C_mH_{2m}-O)_n-R^{12}$ which is unsubstituted or substituted by OH, $-F$, $-Cl$, $-Br$, $-NR^{10}R^{11}$, $C_1-C_{12}$alkyl, $C_1-C_{12}$alkoxy, $C_1-C_{12}$alkylthio-, $-COOR^9$ in which $R^9$ is H or $C_1-C_{18}$alkyl and $R^{10}$ and $R^{11}$, independently of one another, are H, $C_1-C_{18}$alkyl, $-CH_2CH_2OH$, $-CH_2CH(OH)CH_3$, $-CH_2CHOHCH_2OH$, or $-(C_mH_{2m}-O)_n-R^{12}$ in which m is 2 or 3, n is a number from 2 to 6 and $R^{12}$ is H or $C_1-C_{12}$alkyl.

8. A compound according to claim 1, in which $R^1$, $R^4$, $R^5$ and $R^8$ are H, $R^2$, $R^3$ or both are $-SR^{16}$ and $R^6$ and $R^7$ are H, or $R^2$, $R^6$ or $R^7$ are $-SR^{16}$ and $R^3$ and $R^7$ or $R^3$ and $R^6$ are H wherein $R^{16}$ is $C_1-C_{20}$alkyl, $C_2-C_{20}$alkenyl, $C_2-C_{20}$alkynyl, $C_3-C_8$cycloalkyl, $C_6-C_{12}$aryl, $C_7-C_{12}$aralkyl, or $-(C_mH_{2m}-O)_n-R^{12}$ which is unsubstituted or substituted by OH, $-F$, $-Cl$, $-Br$, $-NR^{10}R^{11}$, $C_1-C_{12}$alkyl, $C_1-C_{12}$alkoxy, $C_1-C_{12}$alkylthio-, $-COOR^9$ in which $R^9$ is H or $C_1-C_{18}$alkyl and $R^{10}$ and $R^{11}$, independently of one another, are H, $C_1-C_{18}$alkyl, $-CH_2CH_2OH$, $-CH_2CH(OH)CH_3$, $-CH_2CHOHCH_2OH$, or $-(C_mH_{2m}-O)_n-R^{12}$ in which m is 2 or 3, n is a number from 2 to 6 and $R^{12}$ is H or $C_1-C_{12}$alkyl.

9. A compound according to claim 1, in which $R^1$ and $R^3$ to $R^8$ are H and $R^2$ is the group $R^{16}-S-$ wherein $R^{16}$ is $C_1-C_{20}$alkyl, $C_2-C_{20}$alkenyl, $C_2-C_{20}$alkynyl, $C_3-C_8$cycloalkyl, $C_6-C_{12}$aryl, $C_7-C_{12}$aralkyl, or $-(C_mH_{2m}-O)_n-R^{12}$ which is unsubstituted or substituted by OH, $-F$, $-Cl$, $-Br$, $-NR^{10}R^{11}$, $C_1-C_{12}$alkyl, $C_1-C_{12}$alkoxy, $C_1-C_{12}$alkylthio-, $-COOR^9$ in which $R^9$ is H or $C_1-C_{18}$alkyl and $R^{10}$ and $R^{11}$, independently of one another, are H, $C_1-C_{18}$alkyl, $-CH_2CH_2OH$, $-CH_2CH(OH)CH_3$, $-CH_2CHOHCH_2OH$, or $-(C_mH_{2m}-O)_n-R^{12}$ in which m is 2 or 3, n is a number from 2 to 6 and $R^{12}$ is H or $C_1-C_{12}$alkyl.

10. A compound according to claim 9, in which $R^{16}$ is $C_1-C_{12}$alkyl, $C_6-C_{12}$aryl, $C_7-C_{18}$alkaryl, $-CH_2CH_2OH$, $-CH_2CHOHCH_2OH$, $-CH_2COOR^9$ or $-CH_2CH_2COOR^9$.

* * * * *